United States Patent [19]

Aller et al.

[11] 4,154,825

[45] May 15, 1979

[54] ARYLIMIDOYL PHOSPHORAMIDATES

[75] Inventors: Harold E. Aller, Norristown; Horst O. Bayer, Levittown; Janet Ollinger, North Wales, all of Pa.

[73] Assignee: Rohm and Haas Company, Philadelphia, Pa.

[21] Appl. No.: 745,900

[22] Filed: Nov. 29, 1976

Related U.S. Application Data

[63] Continuation-in-part of Ser. No. 645,053, Dec. 29, 1975, abandoned.

[51] Int. Cl.² ............................ A01N 9/36; C07F 9/24
[52] U.S. Cl. .................................... 424/211; 260/944; 260/940; 260/239 B
[58] Field of Search .......................... 260/944; 424/211

[56] References Cited

U.S. PATENT DOCUMENTS

| | | | |
|---|---|---|---|
| 3,705,218 | 12/1972 | Kishino et al. | 260/964 |
| 3,925,517 | 12/1975 | Pissiotas et al. | 260/944 |
| 3,962,305 | 6/1976 | Pallos | 260/944 X |

*Primary Examiner*—Anton H. Sutto
*Attorney, Agent, or Firm*—Susan Borden Evans

[57] ABSTRACT

This invention relates to novel phosphoramidates of the formula:

$$A-N=C(R)-N(R^1)(P(=X)(OR^2)(SR^3))$$

wherein
A is an optionally substituted ($C_6$-$C_{10}$) aryl group;
R is a hydrogen atom, a ($C_1$-$C_6$) alkyl group, a di($C_1$-$C_4$) alkylamino group, a ($C_4$-$C_6$) cycloamino group, a ($C_1$-$C_6$) alkoxy group, a ($C_1$-$C_6$) alkylthio group or a cyano group;
$R^1$ is (a) an optionally substituted ($C_1$-$C_6$) alkyl group;
  (b) an optionally substituted ($C_3$-$C_8$) cycloalkyl group;
  (c) an optionally substituted ($C_3$-$C_6$) alkenyl group;
  (d) an optionally substituted ($C_5$-$C_8$) cycloalkenyl group;
  (e) a ($C_3$-$C_6$) alkynyl group; or
  (f) an optionally substituted aralkyl group of up to 11 carbon atoms;
$R^2$ is a ($C_1$-$C_6$) alkyl group;
$R^3$ is a ($C_1$-$C_6$) alkyl group; and
X is an oxygen or sulfur atom;
to compositions containing them and to methods of using them to control certain harmful pests.

37 Claims, No Drawings

ARYLIMIDOYL PHOSPHORAMIDATES

This application is a continuation-in-part application of MS application Ser. No. 645,053 filed Dec. 29, 1975 now abandoned.

This invention relates to novel phosphoramidates, to compositions containing them, and to methods of using them to control a variety of harmful pests.

The novel compounds of this invention can be represented by the formula

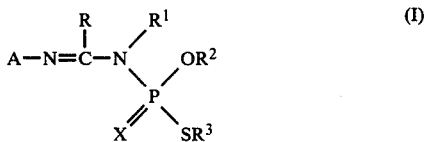

wherein

A is an optionally substituted ($C_6$-$C_{10}$) aryl, preferably optionally substituted phenyl, group;

R is a hydrogen atom, a ($C_1$-$C_6$) alkyl group, a di($C_1$-$C_4$) alkylamino group, a ($C_4$-$C_6$) cycloamino group, a ($C_1$-$C_6$) alkoxy group, a ($C_1$-$C_6$) alkylthio group or a cyano group;

preferably a hydrogen atom, a ($C_1$-$C_4$) alkyl group, a diethylamino group, a ($C_4$-$C_6$) cycloamino group or a ($C_1$-$C_4$) alkoxy; most preferably a hydrogen atom.

$R^1$ is (a) an optionally substituted ($C_1$-$C_6$), preferably ($C_1$-$C_4$), alkyl group;
  (b) an optionally substituted ($C_3$-$C_8$), preferably ($C_5$-$C_7$), cycloalkyl group;
  (c) an optionally substituted ($C_3$-$C_6$), preferably ($C_3$-$C_4$), alkenyl group;
  (d) an optionally substituted ($C_5$-$C_8$), preferably ($C_5$-$C_6$) cycloalkenyl
  (e) a ($C_3$-$C_6$), preferably ($C_3$-$C_4$), alkynyl group; or
  (f) an optionally substituted aralkyl group of up to 11 carbon atoms, preferably a benzyl or phenethyl group;

$R^2$ is a ($C_1$-$C_6$), preferably ($C_1$-$C_4$), alkyl group;

$R_3$ is a ($C_1$-$C_6$), preferably ($C_3$-$C_4$), alkyl group; and

X is an oxygen or sulfur, preferably oxygen, atom.

As used in the specification and claims, the terms alkyl, alkenyl and alkynyl are meant to include branched as well as straight chain alkyl, alkenyl and alkynyl groups. Representative examples of such groups include methyl, ethyl, propyl, isopropyl, sec-butyl, isobutyl, tert-butyl, pentyl, neopentyl, hexyl, allyl, 2-butenyl, 3-methyl-1-pentenyl, 3-hexenyl, propynyl, 1-pentynyl, 4-methyl-1-pentynyl, hexynyl, and the like.

By an optionally substituted ($C_6$-$C_{10}$) aryl group is meant an aryl group such as phenyl or naphthyl, optionally substituted with one or more, but preferably with one to three, substituents selected from the group consisting of alkyl, halogen, haloalkyl, alkoxy, alkylsulfonyl, alkylthio, nitro, cyano, alkoxy carbonyl, dialkylamino, alkylcarbonyl, dialkylaminocarbonyl, phenylthio, and the like, wherein each alkyl moiety is straight or branched chain and contains from 1 to 6, preferably from 1 to 3, carbon atoms; and aryl, aryloxy, arylthio, and the like, wherein the aryl ring contains from 6 to 10, preferably 6, carbon atoms, e.g. phenyl, phenoxy, phenylthio, and the like. The preferred aryl substituents are nitro; halogen, especially chlorine; ($C_1$-$C_4$) alkyl, preferably methyl; ($C_1$-$C_4$) alkoxy, preferably methoxy, and ($C_1$-$C_4$) alkylthio, preferably methylthio.

By an optionally substituted aralkyl group is meant an aralkyl group, e.g. benzyl, phenethyl, 3-phenyl-1-methylpropyl, etc. optionally substituted with one or more, but preferably with one to three substituents selected from the group of substituents defined for substituted ($C_6$-$C_{10}$) aryl above.

By an optionally substituted alkyl group is meant an alkyl group, optionally substituted with one substituent selected from the group consisting of cyano, nitro, furyl, alkoxy, alkylthio, alkylsulfinyl, alkylsulfonyl, alkylcarbonyl, alkoxycarbonyl, alkylcarbonyloxy, mono- or di-alkylaminocarbonyl, dialkylamino and the like, wherein each alkyl moiety is straight or branched chain, and contains from 1 to 6, preferably from 1 to 3, carbon atoms; alkenyloxy and alkenyloxycarbonyl wherein the alkenyl moiety contains from 3 to 6 preferably from 3 to 4 carbon atoms; and aryloxy, arylthio, arylsulfinyl, arylsulfonyl, arylcarbonyl, aryloxycarbonyl, arylcarbonyloxy, arylaminocarbonyl, and the like, wherein the aryl ring contains from 6 to 10, carbon atoms, preferably a phenyl ring, which is optionally substituted (but preferably unsubstituted) with substituents such as defined for substituted ($C_6$-$C_{10}$) aryl above. The preferred alkyl substituents are alkoxycarbonyl, alkylcarbonyl, mono- or di-alkylaminocarbonyl, alkoxy, alkylthio, alkylsulfonyl, phenylthio and cyano.

By an optionally substituted cycloalkyl group is meant a cycloalkyl e.g. cyclopentyl, cyclohexyl, cycloheptyl, etc., optionally substituted with one or more, but preferably with one to three, substituents selected from the group of substituents defined for substituted alkyl above.

By an optionally substituted alkenyl group is meant an alkenyl group optionally substituted with one or more, preferably up to two, substituents selected from the group consisting of cyano, halogen preferably chlorine; alkoxy, preferably methoxy; alkoxycarbonyl, wherein the alkyl moiety is straight or branched chain and contains from 1 to 6, preferably from 1 to 3 carbon atoms, or an optionally substituted ($C_6$-$C_{10}$) aryl group, preferably an unsubstituted phenyl group.

By a cycloamino group is meant a saturated or unsaturated five, six or seven member heterocyclic amino group, containing one or two heteronitrogen atoms and optionally containing a hetero oxygen or sulfur atom, and which is connected to the arylimidoyl moiety through a heteronitrogen atom. Typical cycloamino groups include pyrrolidinyl, piperidenyl, n-morpholinyl, piperazinyl, hexahydroazepinyl, hexahydrodiazepinyl, hexahydrooxazepinyl, etc.

By an optionally substituted cycloalkenyl group is meant a carbocyclic cycloalkenyl group wherein the carbocyclic portion contains from 4 to 8 carbon atoms, preferably from 5 to 7 carbon atoms, e.g. cyclopentenyl, cyclohexenyl, cycloheptenyl, cyclooctenyl, etc., optionally substituted with 1 to 3 substituents selected from the group of substituents defined for substituted alkenyl above.

In the definition of the terms arylthio and aryloxy the aryl moiety contains from 6 to 10 carbon atoms, preferably a phenyl ring, optionally substituted (but preferably unsubstituted) with substituents such as defined for optionally substituted ($C_6$-$C_{10}$) aryl above.

In a preferred embodiment of the invention the A substituent in Formula I has the formula:

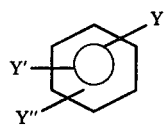 (II)

wherein Y, Y', and Y" are independently a hydrogen atom, a (C$_1$–C$_6$) alkyl group, preferably a methyl group; a halogen atom, preferably a chlorine atom; a (C$_1$–C$_6$) alkoxy group, preferably a methoxy group; a (C$_1$–C$_6$) alkylthio group, preferably a methylthio group; a nitro group; a cyano group; a (C$_1$–C$_6$) preferably (C$_1$–C$_3$) alkoxycarbonyl group; a di(C$_1$–C$_4$) alkylamino group, preferably a dimethylamino group; a (C$_1$–C$_6$) alkyl carbonyl group; a di (C$_1$–C$_4$) alkyl-aminocarbonyl group; an arylthio group, preferably a phenylthio group; or an aryloxy group, preferably a phenoxy group.

The most preferred compounds of this invention possess especially enhanced nematocidal, fungicidal, and arthropodicidal, particularly acaricidal and insecticidal activity. They can be represented by the formula:

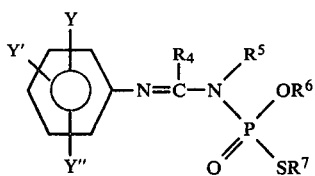

wherein
R$^4$ is a hydrogen atom or a (C$_1$–C$_4$) alkyl;
R$^5$ is a (C$_1$–C$_4$) alkyl group, preferably a methyl or ethyl group, a cyclohexyl group, an C$_3$–C$_4$ alkenyl, a propargyl group, a phenylthio (C$_1$–C$_4$) alkyl group, preferably a phenylthioethyl group, a cyano (C$_1$–C$_4$) alkyl group, preferably a cyanoethyl group, a (C$_1$–C$_4$) alkoxycarbonyl (C$_1$–C$_4$) alkyl group, preferably an ethoxycarbonyl-ethyl group, a furfuryl group or a benzyl group.
R$^6$ is a (C$_1$–C$_4$) alkyl, preferably ethyl, group;
R$^7$ is a (C$_3$–C$_4$) alkyl, preferably n-propyl, isobutyl, or sec-butyl, group; and
Y, Y', Y" are independently hydrogen atoms; (C$_1$–C$_3$) alkyl, preferably methyl, groups; nitro groups, alkylthio, preferably methylthio groups; or halogen, preferably chlorine, atoms. Most preferably hydrogen atoms, methyl groups and chlorine atoms.

Typical examples of compounds within the scope of this invention include the following:

N-butyl O-ethyl S-(1-methylpropyl) N-(N'-phenylformimidoyl) phosphoramidothioate or phosphoramidodithioate N-[N'-(4-chlorophenyl)formimidoyl] O-ethyl N-methyl S-methylethyl phosphoramidothioate or phosphoramidodithioate O-ethyl N-methyl N-[N'-(2,4-dimethylphenyl)acetimidoyl] S-(1-methylpropyl) phosphoramidothioate or phosphoramidodithioate O-methyl S-(2-methylpropyl) N-[N'-(4-nitrophenyl)formimidoyl] N-propyl phosphoramidothioate or phosphoramidodithioate O-ethyl N-(N'-phenylformimidoyl) S-propyl phosphoramidothioate or phosphoramidodithioate O-ethyl S-(1-methylpropyl) N-(2-phenoxyethyl) N-[N'-(3,5-ditrifluoromethylphenyl)formimidoyl] phosphoramidothioate or phosphoramidothioate N-[N'-(4-chloro-2-methylphenyl)formamiodyl] O-ethyl N-methylethyl S-(1-methylpropyl) phosphoramidothioate or phosphoramidodithioate N-[N'-(4-cyanophenyl)formimidoyl] N-ethylthiomethyl O-methyl S-(2-methylpropyl) phosphoramidothioate or phosphoramidodithioate N-[N'-(2,4,6-)acetimidoyl] O-methyl N-(2-methoxyethyl) S-(1-methylpropyl) phosphoramidothioate or phosphoramidodithioate N-ethyl O-ethyl N-[N'-(3-methylphenyl)formimidoyl] S-propyl phosphoramidothioate or phosphoramidodithioate O-ethyl N-methyl N-[N'-(4-methylthiophenyl)formimidoyl] S-propyl phosphoramidodithioate or phosphoramidodithioate N-[N'-(2-chlorophenyl)formimidoyl] N-(2-cyanoethyl) O-methyl S-(2-methylpropyl) phosphoramidothioate or phosphoramidodithioate S-butyl N-methyl O-methyl N-[N'-(2-methyl-4-nitrophenyl) formimidoyl] phosphoramidothioate or phosphoramidodithioate O-ethyl N-[N'-(2-ethylphenyl)formimidoyl] S-(1-methylpropyl) N-propyl phosphoramidothioate or phosphoramidodithioate N-[N'-(4-bromophenyl)formimidoyl] N-(3-chloro-2-propenyl) O-ethyl S-propyl phosphoramidothioate or phosphoramidodithioate N-[N'-(3,4-dichlorophenyl)formimidoyl] O-methyl N-(2-nitrophenyl) S-propyl phosphoramidothioate or phosphoramidodithioate N-[N'-(2-ethoxycarbonylphenyl)formimidoyl] O-ethyl S-(2-methylpropyl) N-propyl phosphoramidothioate or phosphoramidodithioate N-ethyl N-[N'-(4-diethylaminocarbonylphenyl)formimidoyl] O-methyl S-propyl phosphoramidothioate or phosphoramidodithioate O-ethyl S-hexyl N-(3-methylsulfonylpropyl) N-[N'-(4-methylphenyl) formimidoyl] phosphoramidothioate or phosphoramidodithioate N-[N'-(4-chlorophenyl)formimidoyl] O-ethyl N-(2-methylsulfinylethyl) S-propyl phosphoramidothioate or phosphoramidodithioate O-ethyl N-[N'-(4-methoxy-2-methylphenyl)formimidoyl] N-methyl S-propyl phosphoramidothioate or phosphoramidodithioate O-methyl S-(1-methylpropyl) N-(N'-phenylbutanimidoyl) N-phenylthiomethyl phosphoramidothioate or phosphoramidodithioate O-methyl N-[2-(2-methyl-4-methylthiophenoxy)ethyl] N-(N'phenylformimidoyl) S-propyl phosphoramidothioate or phosphoramidodithioate N-benzyl O-ethyl S-(2-methylpropyl) N-(N'-phenylformimidoyl) phosphoramidothioate or phosphoramidodithioate N-(3,5-dichlorobenzyl) N-[N'-(4-chloromethylphenyl) formimidoyl] O-ethyl S-propyl phosphoramidothioate or phosphoramidodithioate N-(2-butenyl) O-ethyl N-(N'-phenylformimidoyl) S-propyl phosphoramidothioate or phosphoramidodithioate N-[N'-(4-acetoxyphenyl)formimidoyl] O-ethyl N-methyl S-propyl phosphoramidothioate or phosphoramidothioate O-ethyl N-[N'-(4-methoxycarbonylphenyl)formimidoyl] S-methylethyl N-(2-naphthoxyethyl) phosphoramidothioate or phosphoramidothioate N-benzenesulfonylmethyl O-ethyl N-(N'-phenylformimidoyl) S-propyl phosphoramidothioate or phosphoramidothioate O-ethyl N-methyl N-[N'-(4-phenylthiophenyl)acetimidoyl] S-propyl phosphoramidothioate or phosphoramidodithioate O-ethyl N-ethylcarbonylmethyl N-[N'-(2-phenoxyphenyl)formimidoyl] S-propyl phosphoramidothioate or phosphoramidodithioate O-butyl N-methyl N-[N'-(4-(2-naphthoxy)phenyl)formimidoyl] S-propyl phosphoramidothioate or phosphoramidodithioate O-ethyl N-methyl N-(N'-phenylpentanimidoyl) S-propyl phosphoramidothioate or phosphoramidodithioate N-[N'-(4-chloro-2-methylphenyl)acetimidoyl] O-ethyl N-methyl S-propyl phosphoramidothioate or phosphoramidodithioate O-ethyl N-methoxycarbonylmethyl N-[N'-(4-methylphenyl)acetimidoyl] S-propyl phosphoramidothioate or phosphoramidodithioate N-[N'-(4-chlorophenyl)acetimidoyl] O-ethyl N-methylaminocarbonylmethyl S-propyl phosphoramidothioate or phosphoramidodithioate O-ethyl N-(2-methylpropyl) S-propyl N-[N'-(4-propylsulfinylphenyl) formimidoyl]phosphoramidothioate or phosphoramidodithioate N-[N'-(2-chloro-4-methylsulfonylphenyl)formimidoyl] O,S-diethyl N-methyl phosphoramidothioate or phosphoramidodithioate N-(2-butynyl) O-ethyl N-[N'-(4-methylcarbonylphenyl)formimidoyl] S-propyl phosphoramidothioate or phosphoramidodithioate N-[N'-(4-biphenyl)formimidoyl] S-methyl N-methylethyl O-(1-methylpropyl) phosphoramidothioate or phosphoramidodithioate O-ethyl N-dimethylaminocarbonylmethyl S-propyl N-(N'-1-naphthylformimidoyl) phosphoramidothioate or phosphoramidodithioate O-ethyl N-[N'-2-(4,6-dichloronaphthyl)formimidoyl] N-[2-(4-chloro) butenyl] S-propyl phosphoramidothioate or phosphoramidodithioate O-ethyl N-(2-ethylsulfinylethyl) N-[(methoxy)(phenylimino)methyl] S-propyl phosphoramidothioate or phosphoramidodithioate N-[(4-methoxycarbonylphenylimino)(hexyloxy)methyl] N-methyl O-methyl S-(1-methylpropyl) phosphoramidothioate or phosphoramidodithioate N-(2-cyanoethyl) N-[(ethoxy)(4-dimethylaminocarbonylphenylimino) methyl] O-ethyl S-(2-methylpropyl) phosphoramidothioate or phosphoramidodithioate N-(2-butenyl) N-[(methoxy) (2-nitrophenylimino)methyl] O-propyl S-propyl phosphoramidothioate or phosphoramidodithioate S-butyl O-ethyl N-[(4-methylthiophenylimino)(propyloxy)methyl] N-(2-propenyl) phosphoramidothioate or phosphoramidodithioate N-[(4-chloro-2-methylphenylimino)(pentyloxy)methyl] N-hexyl O-methyl S-(2-methylpropyl) phosphoramidothioate or phosphoramidodithioate O-ethyl N-[(ethoxy)(3,5-dimethylphenylimino)methyl] N-(2-phenoxyethyl) S-propyl phosphoramidothioate or phosphoramidodithioate N-ethylthiomethyl N-[4-cyanophenylimino)(methoxy)methyl] O-methyl S-(2-methylpropyl) phosphoramidothioate or phosphoramidodithioate N-[(2-chlorophenylimino)(hexylthio)methyl] N-methyl O-methyl S-(1-methylpropyl)phosphoramidothioate or phosphoramidodithioate O-ethyl N-hexyl N-[(methylthio)(4-methylthiophenylimino)methyl] S-propyl phosphoramidothioate or phosphoramidodithioate N-[(4-cyanophenylimino)(ethylthio)methyl] O-methyl S-(2-methylpropyl) N-propyl phosphoramidothioate or phosphoramidodithioate N-(2-cyanoethyl) N-[2-methyl-4-methylsulfonylphenylimino) (propylthio) methyl] O-propyl S-propyl phosphoramidothioate or phosphoramidodithioate N-[(2,4-dichlorophenylimino)(methylthio)methyl] O-methyl S-pentyl N-propyl phosphoramidothioate or phosphoramidodithioate N-(2-butynyl) N-[(2-chloro-4-methylphenylimino)(pentylthio)methyl] O-ethyl S-hexyl phosphoramidothioate or phosphoramidodithioate O-ethyl N-[(2-methoxyphenylimino)(methylthio)methyl] N-(2-methylcarbonylethyl) S-(2-methylpropyl) phosphoramidothioate or phosphoramidodithioate N-[(ethylthio)(4-phenoxyphenylimino)methyl] O-methyl N-(2-phenylthioethyl) S-propyl phosphoramidothioate or phosphoramidodithioate N-(2-butenyl) N-[(2-methyl-4-nitrophenylimino)(propylthio)methyl] O-propyl S-propyl phosphoramidothioate or phosphoramidodithioate N-[(cyano)(4-methylphenylimino)methyl] N-ethyl O-ethyl S-(1-methylpropyl) phosphoramidothioate or phosphoramidodithioate N-[(cyano)(1-naphthylimino)methyl] N-methyl O-propyl S-propyl phosphoramidothioate or phosphoramidodithioate N-[(4-bromo-2-methylphenylimino)(cyano)methyl] O-ethyl N-(2-propenyl) S-propyl phosphoramidothioate or phosphoramidodithioate N[(cyano)(phenylimino)methyl] N-hexyl O-methyl S-(methylethyl) phosphoramidothioate or phosphoramidodithioate O-butyl N-[(cyano)(4-methylcarbonylphenylimino)methyl] N-(2-cyanobutyl) S-(2-methylpropyl) phosphoramidothioate or phosphoramidodithioate N-(2-butenyl) N-[(3-chlorophenylimino)(cyano)methyl] O-ethyl S-propyl phosphoramidothioate or phosphoramidodithioate N-[(dimethylamino)(4-nitrophenylimino)methyl] N-hexyl O-propyl S-propyl phosphoramidothioate or phosphoramidodithioate O-ethyl N-[(dihexylamino)(phenylimino)methyl] N-(2-propenyl) S-propyl phosphoramidothioate or phosphoramidodithioate N-(cyanomethyl) O-ethyl N-[(2-methoxyphenylimino)(methylpropylamino)methyl] S-(1-methylpropyl) phosphoramidothioate or phosphoramidodithioate N-[(dibutylamino)(phenylimino)methyl] O-ethyl N-methyl S-(methylethyl) phosphoramidothioate or phosphoramidodithioate N-ethyl O-ethyl N-[(4-methylthiophenylimino)(piperidino)methyl] S-2-methylpropyl) phosphoramidothioate or phosphoramidodithioate O-ethyl N-[(2,6-dipropylphenylimino)(pyrrolidino)methyl] N-propyl S-propyl phosphoramidothioate or phosphoramidodithioate N-[2-bromo-4-chlorophenylimino)(dimethylamino)methyl] O-ethyl S-hexyl N-pentyl phosphoramidothioate or phosphoramidodithioate N-[(4-butylcarbonylphenylimino)(piperidino)methyl] N-(2-cyanoethyl) O-methyl S-(2-methylpropyl) phosphoramidothioate or phosphoramidodithioate N-[(2,4,6-trichlorophenylimino)(morpholino)methyl] O-ethyl S-hexyl N-(2-phenylthioethyl) phosphoramidothioate or phosphoramidodithioate N-[N'-(4-fluorophenyl)formimidoyl] O-hexyl N-methyl S-propyl phosphoramidothioate or phosphoramidodithioate N-[N'-(4-bromo-2-chlorophenyl)formimidoyl] N-(1-ethylcarbonyloxyethyl) O-ethyl S-(1-methylpropyl) phosphoramidothioate or phosphoramidodithioate O-ethyl N-hexyl N-(N'-phenylformimidoyl) S-propyl phosphoramidothioate or phosphoramidodithioate N-butyl N-[(cyano)(2-phenoxyphenylimino)methyl] O-ethyl S-(1-methylpropyl) phosphoramidothioate or phosphoramidodithioate (1-naphthylimino)methyl] N-methyl O-propyl S-propyl phosphoramidothioate or phosphoramidodithioate N-ethyl O-ethyl N-[(diethylamino)(4-dimethylaminophenylimino)methyl] S-propyl phosphoramidothioate or phosphoramidodithioate N-butyl O-ethyl N-[(2-methylaminocarbonylphenylimino)(pyrrolidino)methyl] S-(1-methylpropyl) phosphoramidothioate or phosphoramidodithioate N-[N'-(2-bromophenyl)formimidoyl] O-ethyl S-ethyl N-2-(4-chlorophenoxycarbonyl)ethyl phosphoramidothioate or phosphoramidodithioate O-ethyl N-(2-diethylamino)ethyl N-(N'-phenylformimidoyl) S-propyl phosphoramidothioate or phosphoramidodithioate O-methyl S-methyl N-2-(4-methylphenylcarbonyloxy)propyl N-[N'-(2-methylthiophenyl)acetimidoyl] phosphoramidothioate or phosphoramidodithioate O-butyl N-[(dimethylamino)(2-methoxycarbonylphenylimino)methyl] S-propyl N-2-(2-propylphenylsulfinyl)ethyl phosphoramidothioate or phosphoramidodithioate O-ethyl N-[(diethylamino)(phenylimino)methyl] N-phenylaminocarbonylmethyl S-propyl phosphoramidothioate or phosphoramidodithioate O-ethyl N-furylmethyl N-[N'-(4-nitrophenyl)acetimidoyl] S-propyl phosphoramidothioate or phosphoramidodithioate N-(3-cyano-2-propenyl) O-ethyl N-[N'-(2-methylphenyl)acetimidoyl] S-(2-methylpropyl)phosphoramidothioate or phosphoramidodithioate N-[N'-(2-bromophenyl)formimidoyl] N-(2-methyl-3-methoxycarbonyl-2-propenyl) O-pentyl S-propyl phosphoramidothioate or phosphoramidodithioate O-ethyl N-[N'-(2-ethylphenyl)acetimidoyl] S-(1-methylpropyl) N-2-(2-propenyloxycarbonyl)propyl phosphoramidothioate or phosphoramidodithioate O-methyl S-(methylethyl) N-[3-(4-methylphenyl)-2-propenyl] N-[N'-(4-methylthiophenyl)formimidoyl] phosphoramidothioate or phosphoramidodithioate O-butyl N-[3-(2-naphthyl)-2-propenyl] N-[N'-(4-nitrophenyl)formimidoyl] S-propyl phosphoramidothioate or phosphoramidodithioate N-[N'-(3-bromophenyl)formimidoyl] O-ethyl N-[2-(4-nitrophenyl)ethyl] S-propyl phosphoramidothioate or phosphoramidodithioate N-(3-cyanopentyl) O-methyl S-methyl N-(N'-phenylformimidoyl)phosphoramidothioate or phosphoramidodithioate N-cycloheptyl N-[N'-(4-ethoxycarbonylphenyl)acetimidoyl] O-ethyl S-propyl phosphoramidothioate or phosphoramidodithioate N-(4-cyano-2-cyclohexenyl) O-methyl S-(2-methylethyl) N-[(phenylimino)(propoxylmethyl] phosphoramidothioate or phosphoramidodithioate N-(4-chloro-3-cycloheptenyl) O-ethyl S-(methylethyl) N-[(2-methylphenylimino)(pentyloxy)methyl] phosphoramidothioate or phosphoramidodithioate N-butyl O-ethyl N-[(4-methoxycarbonylphenylimino)(piperazinyl)methyl] S-propyl phosphoramidothioate or phosphoramidodithioate N-[(hexahydroazepinyl)(phenylimino)methyl] N-methyl O-propyl S-propyl phosphoramidothioate or phosphoramidodithioate N-ethyl O-ethyl N-[(hexahydrooxazepinyl)(4-propylphenylimino)methyl] S-(1-methylpropyl) phosphoramidothioate or phosphoramidodithioate The compounds of the present invention can be prepared by a variety of methods. One method involves reacting an amidine with an O,S-dialkyl phosphorochloridothioate or phosphorochloridodithioate in the presence of an acid binding agent. The general reaction can be represented by the following equation:

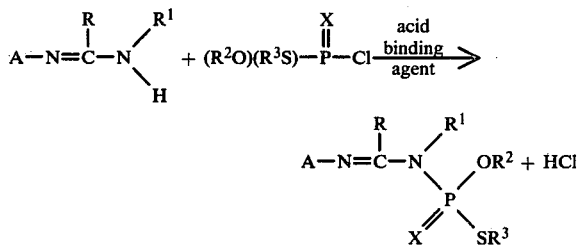

wherein A, R, R$^1$, R$^2$, R$^3$, and X are as defined for Formula I.

Representative acid binding agents include tertiary amines such as trialkylamines and dialkylanilines, and inorganic bases such as hydrides, hydroxides, carbonates and bicarbonates of alkali and alkaline earth metals. Generally, a substantially equimolar ratio of reactants is preferred but an excess of either of the reactants can be employed. While not required, the reaction is advantageously carried out in the presence of an inert organic solvent such as an ether, aromatic hydrocarbon, halogenated aromatic hydrocarbon, aliphatic hydrocarbon, aliphatic ketone, aliphatic nitrile, and the like, or mixtures thereof. Suitable solvents include, for example, ethyl ether, dioxane, tetrahydrofuran, benzene, toluene, chlorobenzene, heptane, methylethyl ketone, acetone, acetonitrile, and the like. The reaction is generally conducted in a temperature range of about −10° to 100° C. or more, and preferably in the range of about 0° to about 60° C.

All of the starting materials used in the preparation of the compounds of this invention are known compounds or are readily prepared by adaptations of known routes. For example, the formamidine starting materials are prepared by condensation of an aniline with an N-alkyl formamide. (U.S. Pat. No. 3,502,720, Belgian Pat. No. 771,792, South African Pat. No. 732,129.) The O,S-dialkylphosphorochloridothioates are prepared for example by reacting an alkylsulfenyl chloride with a dialkylchlorophosphite [A. F. Lippman, J. Org. Chem., 30, 3217 (1965)].

The following examples are given by way of illustration and are not to be considered as limitations of the present invention.

EXAMPLE 1—Preparation of O-ethyl N-methyl N-[N'-(2,4-dimthylphenyl)formimidoyl] S-propyl phosphoramidothioate A solution of O-ethyl S-propyl phosphorochloridothioate, 2.5 g. (0.0124 mole), in 10 ml. of tetrahydrofuran (THF) is added dropwise to a solution of N-methyl-N'-(2,4-dimethylphenyl)formamidine, 2.0 g. (0.0124 mole) and triethylamine, 1.25 g. (0.0124 mole), in 25 ml. of THF at room temperature. The reaction is stirred for one hour at room temperature, diluted with 70 ml. of ether, filtered to remove triethylamine hydrochloride, and evaporated by vacuum stripping to give 4.2 g. of orange oil which is chromatographed on 65 g. of 60–200 mesh silica gel. Elution with 900 ml. of 7% ether in benzene (discarding the first two 50 ml. fractions) and concentration under vacuum gives 2.6 g. (64% of theory) of purified product as an orange oil.

EXAMPLE 2—Preparation of N-cyclohexyl O-ethyl N-[N'-phenylformimidoyl] S-propyl phosphoramidothioate A solution of O-ethyl S-propyl phosphorochloridothioate, 2.02 g. (0.0099 mole), in 5 ml. of THF is added dropwise to an ice-cooled solution of N-cyclohexyl-N'-phenyl formamidine, 2.0 g. (0.0099 mole), and triethylamine, 1.01 g. (0.01 mole), in 25 ml. of THF. The reaction is stirred one hour at room temperature, diluted with 60 ml. of ether, filtered to remove triethylamine hydrochloride, and evaporated by vacuum stripping to give 3.8 g. of yellow oil which is chromatographed on 40 g. of 60–200 mesh silica gel. Elution with 350 ml. of 10% ether in benzene (discarding the first 200 ml. fraction) gives 0.44 g. (12% of theory) of purified product as an oil.

EXAMPLE 3—Preparation of O-ethyl N-[N'-phenylformimidoyl] N-(2-propenyl) S-propyl phosphoramidothioate A solution of O-ethyl S-propyl phosphorochloridothioate, 3.16 g. (0.016 mole), in 10 ml. of THF is added dropwise to an ice-cooled solution of triethylamine, 1.58 g. (0.016 mole), and N-allyl-N'-phenyl formamidine, 2.5 g. (0.016 mole) in 30 ml. of THF. The reaction is stirred one and one-half hours at room temperature, diluted with 100 ml. of ether, filtered to remove the triethylamine hydrochloride, and evaporated by vacuum stripping to give 5.6 g. of yellow oil which is chromatographed on 60 g. of 60–200 mesh silica gel. Elution with 510 ml. of 10% ether in benzene (discarding the first 210 ml.) gives 1.7 g. (33% of theory) of purified product as an oil.

EXAMPLE 4—Preparation of N-[N'-(4-chlorophenylformimidoyl)] N-(2-cyanoethyl) O-ethyl S-(1-methylpropyl) phosphoramidothioate A solution of O-ethyl S-(1-methyl phosphorochloridothioate, 1.78 g. (0.008 mole), in 10 ml. of THF is added dropwise to an ice-cooled solution of N-(2-cyanoethyl)-N'-(4-chlorophenyl) formamidine, 1.7 g. (0.008 mole), and triethylamine, 0.82 g. (0.008 mole), in 25 ml. of THF. The reaction is stirred one hour at room temperature, diluted with 100 ml. of ether, filtered to remove the triethylamine hydrochloride, and evaporated by vacuum stripping to give 3.4 g. of yellow oil which is chromatographed on 60 g. of Biosil A. Elution with 350 ml. of 10% ether in benzene (discarding the first 300 mls.) gives 0.6 g. (19% of theory) of purified product.

EXAMPLE 5—Preparation of O-ethyl N-[(diethylamino)imino)methyl] N-(2-propenyl) S-propyl phosphoramidothioate A solution of O-ethyl S-propyl phosphorochloridothioate, 6.07 g. (0.03 mole), in 15 ml. of THF is added dropwise to an ice-cooled solution of N-allyl-2-diethylamino-N'-phenyl formamidine, 6.8 g. (0.029 mole) and triethylamine, 4.55 g. (0.045 mole), in 35 ml. of THF. The reaction is stirred 2 hr. at room temperature and filtered to remove the triethylamine hydrochloride. The filtrate was evaporated by vacuum stripping, and 20 ml. of ether and 1 ml. of triethylamine are added. This mixture is stirred one and one-half hours, filtered to remove the triethylamine hydrochloride and evaporated by vacuum stripping to give 10.2 g. of orange oil, 6 g. of which is chromatographed on Biosil A. Elution with ether gives 2.99 g. (44% of theory) of purified product.

EXAMPLE 6—Preparation of N-ethyl O-ethyl N-[(methoxy)(phenylimino)methyl]S-propyl phosphoramidothioate O-Ethyl S-propyl phosphorochloridothioate, 4.1 g. (0.02 mole), is added dropwise to an ice-cooled solution of N-ethyl-2-methoxy-N'-phenyl formamidine, 3.6 g. (0.02 mole), and triethylamine, 2.1 g. (0.02 mole), in 130 ml. of THF. The reaction is stirred overnight at room temperature, filtered to remove the triethylamine hydrochloride, and evaporated by vacuum stripping to give an oil which is chromatographed on 90 g of Biosil A. Elution with 450 ml. of 10% ether in hexane (discarding the first 350 ml Fraction) and 350 ml. of 20% ether in hexane gives 0.5 g. (7% of theory) of purified product.

Additional examples of the compounds embraced by Formula I, which are prepared in a manner analogous to the foregoing Examples, are listed as Examples 1 to 84 in Table I.

TABLE I

ELEMENTAL ANALYSIS

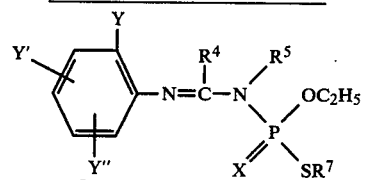

| Ex. No. | R4 | R5 | R7 | Y | Y' | Y" | X | C | H | N |
|---|---|---|---|---|---|---|---|---|---|---|
| 1 | H | CH3 | C3H7-n | CH3 | 4-CH3 | H | O | 54.8(55.0) | 7.62(7.80) | 8.53(9.23) |
| 2 | H | CH3 | C3H7-n | Cl | 4-CH3 | H | O | 48.2(47.8) | 6.32(6.08) | 8.04(8.12) |
| 3 | H | CH3 | C3H7-n | CH3 | 4-Cl | H | O | 48.2(48.4) | 6.32(6.42) | 8.04(8.36) |
| 4 | H | CH3 | C3H7-n | H | H | H | O | 51.9(50.7) | 7.00(7.08) | 9.34(9.08) |
| 5 | H | CH3 | C3H7-n | H | 4-Cl | H | O | 46.5(46.7) | 5.98(6.02) | 8.37(8.59) |
| 6 | H | CH3 | C3H7-n | H | 4-CH3 | H | O | 53.5(53.0) | 7.33(7.39) | 8.92(8.35) |
| 7 | H | CH3 | C3H7-n | Cl | 4-Cl | H | O | 42.3(41.9) | 5.15(5.27) | 7.58(7.32) |
| 8 | H | CH3 | C3H7-n | CH3 | H | H | O | 53.5(53.3) | 7.33(7.79) | 8.92(10.3) |
| 9 | H | CH3 | C4H9-iso | CH3 | 4-Cl | H | O | 49.5(51.2) | 6.62(7.10) | 7.72(7.41) |
| 10 | H | CH3 | C4H9-sec | CH3 | 4-Cl | H | O | 49.5(50.8) | 6.62(6.85) | 7.72(7.44) |
| 11 | H | CH3 | C3H7-n | CH3 | H | 2-Cl | O | 48.2(47.7) | 6.32(6.19) | 8.04(8.12) |
| 12 | H | C2H5 | C3H7-n | CH3 | 4-Cl | H | O | 49.6(48.9) | 6.61(6.45) | 7.71(6.60) |
| 13 | H | C2H5 | C4H9-sec | CH3 | 4-Cl | H | O | 51.0(51.3) | 6.89(6.72) | 7.44(7.45) |
| 14 | H | CH3 | C3H7-n | CH3 | 4-NO2 | H | O | 46.8(46.5) | 6.12(6.44) | 11.7(11.2) |
| 15 | H | CH3 | C3H7-n | CH3 | 4-Cl | 6-CH3 | O | 49.5(49.6) | 6.62(6.76) | 7.72(7.67) |
| 16 | H | CH3 | C3H7-n | Cl | 4-Cl | 6-CH3 | O | 43.9(44.2) | 5.48(5.74) | 7.31(7.43) |
| 17 | CH3 | CH3 | C3H7-n | H | H | H | O | 53.5(53.6) | 7.32(7.57) | 8.92(8.76) |
| 18 | CH3 | CH3 | C3H7-n | H | 4-CH3 | H | O | 54.8(54.7) | 7.62(7.86) | 8.54(8.39) |
| 19 | CH3 | CH3 | C3H7-n | H | 4-Cl | H | O | 48.2(47.7) | 6.31(6.51) | 8.02(7.85) |
| 20 | H | CH3 | C4H9-iso | H | H | H | O | 53.5(53.5) | 7.32(7.44) | 8.91(8.15) |
| 21 | H | C2H5 | C3H7-n | H | H | H | O | 53.5(54.0) | 7.32(7.58) | 8.92(8.88) |
| 22 | CH3 | CH3 | C3H7-n | CH3 | 4-Cl | H | O | 49.6(48.1) | 6.63(6.87) | 7.72(6.88) |
| 23 | H | C3H7-iso | C3H7-n | H | H | H | O | 54.8(53.5) | 7.62(7.61) | 8.53(7.25) |
| 24 | H | C3H7-n | C3H7-n | H | H | H | O | 54.8(54.8) | 7.62(7.83) | 8.53(8.25) |
| 25 | H | CH2CH=CH2 | C3H7-n | H | H | H | O | 55.2(56.6) | 7.05(7.40) | 8.60(9.06) |
| 26 | H | cyclohexyl | C3H7-n | H | H | H | O | 58.7(59.3) | 7.88(8.39) | 7.60(7.90) |
| 27 | H | CH3 | C3H7-n | H | 4-SCH3 | H | O | 46.8(50.2) | 6.64(7.11) | 8.08(8.10) |
| 28 | H | C2H5 | C4H9-iso | H | H | H | O | 54.9(55.4) | 7.67(7.87) | 8.53(8.50) |
| 29 | H | C4H9-n | C3H7-n | H | H | H | O | 56.2(56.4) | 7.89(7.86) | 8.19(7.99) |
| 30 | H | C2H5 | C3H7-n | CH3 | 4-CH3 | H | O | 55.8(56.3) | 7.90(7.96) | 8.13(8.08) |
| 31 | H | C2H5 | C3H7-n | CH3 | H | H | O | 54.8(55.9) | 7.67(7.67) | 8.53(8.65) |
| 32 | H | CH3 | C3H7-n | H | 4-Cl | 3-Cl | O | 42.3(42.7) | 5.18(5.09) | 7.58(7.68) |
| 33 | H | C2H5 | C4H9-sec | H | H | H | O | 54.8(54.9) | 7.62(7.71) | 8.54(8.91) |
| 34 | H | C2H5 | C2H5 | H | H | H | O | 52.0(51.9) | 7.00(7.24) | 9.34(9.31) |
| 35 | H | C2H5 | C4H9-n | H | H | H | O | 54.9(55.1) | 7.67(8.19) | 8.53(8.69) |
| 36 | H | CH3 | C4H9-sec | H | H | H | O | 53.5(53.0) | 7.37(7.67) | 8.91(9.37) |
| 37 | H | CH3 | C4H9-n | H | H | H | O | 53.5(53.2) | 7.37(7.82) | 8.91(9.19) |
| 38 | H | CH3 | C3H7-n | H | 3-Cl | 5-Cl | O | 42.3(42.7) | 5.18(4.89) | 7.58(7.81) |
| 39 | H | CH3 | C4H9-sec | H | 4-Cl | H | O | 48.2(48.3) | 6.36(6.37) | 8.03(8.04) |
| 40 | H | CH3 | C4H9-sec | Cl | 4-Cl | H | O | 43.9(44.3) | 5.52(5.54) | 7.31(7.73) |
| 41 | H | C2H5 | C4H9-sec | H | 4-Cl | H | O | 49.7(49.8) | 6.66(6.73) | 7.72(7.82) |
| 42 | H | C2H5 | C3H7-n | H | 4-Cl | H | O | 48.2(48.6) | 6.36(6.46) | 8.03(8.25) |
| 43 | H | C2H5 | C4H9-sec | Cl | 4-Cl | H | O | 45.3(45.4) | 5.83(5.92) | 7.05(6.64) |
| 44 | H | C2H5 | C3H7-n | H | 4-Me | H | O | 54.9(54.8) | 7.67(7.64) | 8.56(8.16) |
| 45 | H | C2H5 | C4H9-sec | H | 4-SCH3 | H | O | 51.3(52.9) | 7.22(7.59) | 7.49(8.00) |
| 46 | H | C2H5 | C3H7-n | H | 4-SCH3 | H | O | 50.0(52.0) | 6.94(7.34) | 7.78(8.34) |
| 47 | H | CH3 | C4H9-sec | CH3 | H | H | O | 54.8(56.1) | 7.62(8.15) | 8.54(9.35) |
| 48 | H | CH2CH=CH2 | C4H9-sec | H | H | H | O | 56.4(56.5) | 7.40(7.50) | 8.23(8.26) |
| 49 | H | CH2CH=CH2 | C3H7-n | H | 4-Cl | H | O | 49.9(50.5) | 6.10(5.90) | 7.78(7.77) |
| 50 | H | CHCH CH2 | C4H9-sec | H | 4-Cl | H | O | 51.3(51.9) | 6.40(6.38) | 7.46(7.87) |
| 51 | H | CH2CH=CH2 | C4H9-iso | H | H | H | O | 56.7(56.5) | 7.08(7.59) | 8.25(8.56) |
| 52 | H | CH2CH=CH2 | C4H9-sec | CH3 | 4-Cl | H | O | 52.5(51.6) | 6.74(6.70) | 7.21(6.75) |
| 53 | H | CH2CH=CH2 | C3H7-n | CH3 | 4-Cl | H | O | 51.3(51.6) | 6.45(6.66) | 7.47(7.20) |
| 54 | H | CH2CH=CH2 | C4H9-sec | H | 4-SCH3 | H | O | 52.8(53.8) | 7.04(7.36) | 7.26(7.89) |
| 55 | H | CH2CH=CH2 | C3H7-n | H | 4-SCH3 | H | O | 51.6(51.6) | 6.76(7.05) | 7.52(7.59) |
| 56 | H | CH2CH=CH2 | C4H9-iso | CH3 | 4-Cl | H | O | 52.5(54.9) | 6.74(6.99) | 7.21(8.02) |
| 57 | H | CH2C(CH3)=CH2 | C3H7-n | H | H | H | O | 56.4(55.4) | 7.36(7.92) | 8.23(8.24) |
| 58 | H | CH2C(CH3)=CH2 | C4H9-sec | H | H | H | O | 57.6(56.2) | 7.64(7.92) | 7.91(8.49) |
| 59 | H | CH2C≡CH | C4H9-sec | H | 4-Cl | H | O | 51.5(51.2) | 5.91(5.71) | 7.51(7.56) |
| 60 | H | CH2C≡CH | C3H7-n | H | 4-Cl | H | O | 50.1(50.5) | 5.88(5.71) | 7.79(8.26) |
| 61 | H | CH2C≡CH | C3H7-n | H | H | H | O | 55.6(55.6) | 6.48(6.54) | 8.64(9.33) |
| 62 | H | CH2C≡CH | C4H9-n | H | H | H | O | 56.8(56.9) | 6.81(7.23) | 8.28(8.65) |
| 63 | H | CH(CH3)CO2C2H5 | C3H7-n | H | H | H | O | 52.8(53.5) | 7.04(7.29) | 7.25(7.60) |
| 64 | H | C2H4SC6H5 | C3H7-n | H | H | H | O | 56.9(56.7) | 6.44(6.12) | 6.63(7.01) |
| 65 | H | CH(CH3)CO2C2H5 | C4H9-sec | H | H | H | O | 54.0(54.1) | 7.30(7.53) | 7.00(7.04) |
| 66 | H | CH(CH3)CO2C2H5 | C3H7-n | H | 4-Cl | H | O | 48.5(48.5) | 6.23(6.50) | 6.66(6.81) |
| 67 | H | C2H4C≡N | C3H7-n | H | H | H | O | 53.1(51.6) | 6.53(6.54) | 12.4(11.8) |
| 68 | H | CH(CH3)CO2C2H5 | C3H7-n | H | H | H | O | 52.8(53.5) | 7.04(7.29) | 7.25(7.60) |
| 69 | H | CH(CH3)CO2C2H5 | C4H9-iso | H | 4-Cl | H | O | 49.7(48.7) | 6.49(6.49) | 6.44(6.31) |
| 70 | H | CH(CH3)CO2C2H5 | C4H9-sec | H | 4-Cl | H | O | 49.7(50.4) | 6.49(6.50) | 6.44(7.22) |

TABLE I-continued
ELEMENTAL ANALYSIS

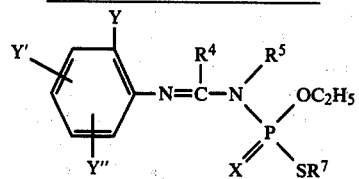

| Ex. No. | $R^4$ | $R^5$ | $R^7$ | Y | Y' | Y'' | X | C | H | N |
|---|---|---|---|---|---|---|---|---|---|---|
| 71 | H | $CH_2-\langle O \rangle$ | $C_3H_7$-n | H | H | H | O | 55.7(55.9) | 6.32(6.35) | 7.65(7.75) |
| 72 | H | $C_2H_4C{\equiv}N$ | $C_4H_9$-sec | H | 4-Cl | H | O | 49.6(48.1) | 5.13(6.19) | 10.8(9.04) |
| 73 | H | $C_2H_4C{\equiv}N$ | $C_3H_7$-n | H | 4-Cl | H | O | 48.2(49.1) | 5.62(5.94) | 11.2(11.4) |
| 74 | $CH_3$ | $CH_3$ | $C_4H_9$-sec | H | 4-Cl | H | O | 49.7(49.7) | 6.66(6.70) | 7.72(7.45) |
| 75 | $CH_3$ | $CH_3$ | $C_4H_9$-sec | H | 4-Me | H | O | 56.1(56.0) | 7.95(8.14) | 8.18(7.76) |
| 76 | $CH_3$ | $CH_3$ | $C_2H_5$ | H | 4-Cl | H | O | 46.6(46.9) | 6.02(5.90) | 8.37(8.39) |
| 77 | $CH_3$ | $CH_3$ | $C_4H_9$-iso | H | 4-Cl | H | O | 49.7(50.0) | 6.67(6.59) | 7.72(7.56) |
| 78 | $CH_3$ | $CH_3$ | $C_3H_7$-n | Cl | 4-Cl | H | O | 43.9(43.7) | 5.52(5.59) | 7.31(7.74) |
| 79 | H | $CH_3$ | $C_3H_7$-n | H | H | H | S | 49.4(50.3) | 6.64(7.18) | 8.86(9.28) |
| 80 | $N(CH_2CH_3)_2$ | $CH_2CH{=}CH_2$ | $C_3H_7$-n | H | H | H | O | 57.4(57.9) | 8.13(8.25) | 10.6(10.1) |
| 81 | H | $CH_2CH_2N(CH_3)_2$ | $C_3H_7$-n | H | H | H | O | 53.7(49.98) | 7.83(7.77) | 11.8(11.2) |
| 82 | H | $C_2H_4C{\equiv}N$ | $C_4H_9$-sec | H | H | H | O | 54.4(54.8) | 6.84(7.09) | 11.9(12.3) |
| 83 | $OCH_3$ | $C_2H_5$ | $C_3H_7$-n | H | H | H | O | 52.3(52.5) | 7.76(7.41) | 8.13(8.28) |
| 84 | $N(CH_2CH_3)_2$ | $C_2H_5$ | $C_3H_7$-n | H | 4-Me | H | O | 57.4(56.9) | 8.11(8.20) | 10.6(10.6) |

The compounds of the invention are useful for the protection of plants and animals, including mammals, from the ravages of harmful and annoying pests. These compounds are particularly effective against arthropods (in varying stages of development) and are especially effective against members of the Class Arachnoidea, which includes the Order Acarina, as represented by mites and ticks, and the Class Insecta, the insects. Among the arthropods which are effectively controlled by the compounds of the present invention are the chewing insects, e.g. the southern armyworm (*Spodoptera eridania*), the sucking insects, e.g. the green peach aphid (*Myzus persicae*), soil-dwelling insects, e.g. the southern corn rootworm (*Diabrotica undecimpunctata howardi*), houseflies, mites, e.g. the two-spotted spider mite (*Tetranychus urticae*), and others.

The compounds of this invention are also active as fungicides, e.g. as phytopathogenic fungicides. Some of the plant fungicidal diseases controlled by compounds of this invention include, for example, rice blast (*Piricularia oryzae*), bean powdery mildew (*Erysiphe polygoni*), grape downy mildew (*Plasmopara viticola*) and the like.

Furthermore, compounds of this invention, particularly i.e. compounds wherein R in Formula I is a hydrogen atom, possess nematocidal activity. Among the nematodes which are effectively controlled by the compounds of the present invention are soil nematodes, typified by the southern root knot nematode (*Meloidognye incognita*).

Generally, control of pests is achieved in accordance with this invention by application of the compounds in pesticidally effective amounts (e.g. arthropodicidally effective amounts) either directly to the pests to be controlled or to the loci to be freed of or protected from attach by such pests. Plant protection loci may be defined as the aerial and subterranean portions of plants or propagative subunits and their immediate or future environs. For example, food, fiber, forage, forest, and ornamental crops and stored products thereof represent plant protection loci. Treatment with compounds of this invention of domestic animals, and their immediate environs similarly constitute representative loci for protection against various annoying ectoparasitic or endoparasitic Acarina (Acari) and Insecta. Many of the above formulations can be utilized on animals in the control of parasite. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reducing in number or any combination thereof.

The term "pest" as employed in the specification and claims of this application refers to fungi, nematodes and various arthropods especially insects and acarids.

The phosphoramidates of this invention possess general utility as arthropodicides, particularly against members of the class Arachnoidea, which includes the order Acarina, as represented by mites and ticks, and Insecta, the insects. Certain compounds of this invention are also active as nematocides and fungicides, particularly phytopathogenic fungicides.

Initial evaluations are made on the following mite, insects, and nematode:

| Code Symbol | Common Name | Latin Name |
|---|---|---|
| TSM | Two-spotted spider mite | *Tetranychus urticae* |
| GPA | Green peach aphis | *Myzus persicae* |
| MBB | Mexican bean beetle | *Epilachna varivestis* |
| SAW | Southern armyworm | *Spodoptera eridania* |
| CRW | Southern corn rootworm, ova and larvae | *Diabrotica undecimpunctata howardi* |
| nema | Southern root-knot nematode | *Meloidogyne incognita* |
| HF | House fly | *Musca domestica* |
| RB | Rice blast | *Piricularia oryzae* |

A test solution containing 600 ppm of test compound can be made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyl resin (commercially available under the trademark Triton B-1956) can be utilized at the equivalent of one ounce per 100 gallons of test solution as a surfactant.

For the mite test, infested bean (*Phaseolus limeanus*) leaf discs (1.25 inches in diameter) containing about 50 mites and for green peach aphid tests, infested brocoli (*Brassica oleracea italica*) leaves or portions thereof containing about 50 aphids are placed in a Petri dish lid on a moistened piece of cotton. The leaves are then sprayed with the test solution using a rotating turntable. They are held for 24 hours and then the percent kill is determined.

For the bean beetle and armyworm test, detached bean leaves on pieces of moistened filter paper are sprayed as above for the mite test in similar dishes and allowed to dry. One such dish is infested with 10 third instar Mexican bean beetle larvae, while another is infested with 10 third instar southern armyworm larvae. The dishes are covered. After holding for 48 hours, the percent kill is obtained.

For the house fly tests, half pint glass canning jars with a screened top are used. Food is supplied for the house fly (sugar water). The test insects consist of 20 adult house flies. The jars containing the insects are sprayed using the turntable. In the house fly test, a percent knockdown is determined one hour after application, the percent kill after 24 hours.

For the nematode test, soil is homogeneously inoculated with a macerated blend of tomato roots heavily knotted with the root knot nematode. Ten milliliters of the test solution are added to 200 milliliters of the inoculated soil in a 16 oz. jar to give a concentration by volume of about 30 ppm. The jar is then shaken to insure thorough mixing, immediately uncapped, and allowed to air for 24 hours. The soil is then placed into a 3 inch plastic pot after which time 3 cucumber (*Cucumis sativus*) seeds are planted. About 23 days thereafter, the cucumber plants are removed from the soil and the root system examined for the presence of knots. A total of 25 knots or less is considered as a measure of control.

Ovicidal and larvicidal tests are conducted on representative compounds of this invention. These compounds demonstrate ovicidal and larvicidal activity.

For tests involving the southern corn rootworm (*Diabrotica undecimpunctata howardi*) ova and larvae, two layers of 4.25 cm. filter papers are placed in small, Petri dishes, and sprayed on the turntable with a 600 ppm solution of the test compound and air dried. About 100 eggs in about one milliliter of water are pipetted onto the filter paper and the dishes covered. These are held for 6 days and examined under the microscope. The percent kill values for ova and larvae are determined.

Fungicidal evaluation of compounds of this invention is carried out by way of a foliar screening test. The general procedure for the fungicidal test is to take potted plants in proper condition of growth for susceptibility to the plant diseases to be evaluated, to spray these on a moving belt and allow them to dry. The plants are then inoculated with the respective fungal spores and allowed to incubate until the disease symptoms and the disease control are read or estimated. Percentage of disease control is recorded.

Compounds of the present invention are tested at a concentration of 300 ppm in a solution or suspension made by dissolving a weighed amount of the candidate fungicide in a 50:50 mixture of acetone and methanol and then adding an equal volume of water.

Table II gives the results of the foregoing biological evaluations.

TABLE II

| Example No. | TSM[b] | GPA[b] | MBB[b] | SAW[b] | CRW E/L[c] | Nema[d] | HF[b] | RB[e] |
|---|---|---|---|---|---|---|---|---|
| 1 | 100 | 100 | 100 | 100 | 67/100 | A | 100 | — |
| 2 | 100 | 100 | 100 | 100 | 0/89 | A | 100 | A |
| 3 | 100 | 100 | 100 | 100 | 49/90 | A | 100 | A |
| 4 | 100 | 100 | 100 | 100 | 0/87 | A | 100 | A |
| 5 | 100 | 100 | 100 | 100 | 0/83 | A | 100 | A |
| 6 | 100 | 100 | 100 | 100 | 58/95 | A | 100 | A |
| 7 | 100 | 100 | 100 | 100 | 0/70 | A | 100 | — |
| 8 | 100 | 100 | 100 | 100 | 0/96 | A | 100 | E |
| 9 | 100 | 100 | 100 | 100 | 55/92 | A | 100 | B |
| 10 | 100 | 100 | 100 | 100 | 76/100 | A | 100 | A |
| 11 | 100 | 100 | 100 | 100 | 73/95 | A | 100 | A |
| 12 | 100 | 100 | 100 | 100 | 0/98 | A | 100 | — |
| 13 | 100 | 100 | 100 | 100 | 0/98 | A | 100 | A |
| 14 | 100 | 100 | 100 | 100 | 0/93 | A | 100 | — |
| 15 | 100 | 100 | 100 | 100 | 43/100 | A | 100 | — |
| 16 | 100 | 100 | 100 | 100 | 0/100 | A | 100 | — |
| 17 | 100 | 100 | 100 | 100 | 50/100 | C | 100 | — |
| 18 | 100 | 100 | 100 | 100 | 47/93 | C | 100 | — |
| 19 | 100 | 100 | 100 | 100 | 59/100 | C | 100 | — |
| 20 | 100 | 100 | 100 | 100 | 60/100 | A | 100 | — |
| 21 | 100 | 100 | 100 | 100 | 48/100 | A | 100 | B |
| 22 | 100 | 100 | 100 | 100 | 0/100 | C | 100 | — |
| 23 | 100 | 100 | 100 | 100 | 67/100 | A | 100 | — |
| 24 | 100 | 100 | 100 | 100 | 90/100 | A | 100 | B |
| 25 | 100 | 100 | 100 | 100 | 77/100 | A | 100 | — |
| 26 | 100 | 100 | 100 | 100 | 81/100 | C | 100 | — |
| 27 | 100 | 100 | 100 | 100 | 63/86 | A | 100 | — |
| 28 | 100 | 100 | 100 | 100 | 96/100 | A | 100 | — |
| 29 | 100 | 100 | 100 | 100 | 46/100 | A | 100 | — |
| 30 | 100 | 100 | 100 | 100 | 58/100 | A | 100 | — |
| 31 | 100 | 100 | 100 | 100 | 61/100 | A | 100 | — |
| 32 | 100 | 100 | 100 | 100 | 0/00 | A | 100 | — |
| 33 | 100 | 100 | 100 | 100 | 78/100 | A | 100 | — |
| 34 | 100 | 100 | 100 | 100 | 0/74 | A | — | — |
| 35 | 100 | 100 | 100 | 100 | 71/100 | A | — | — |
| 36 | 100 | 100 | 100 | 100 | 78/100 | A | 100 | E |

TABLE II-continued

| Example No. | TSM[b] | GPA[b] | MBB[b] | SAW[b] | CRW E/L[c] | Nema[d] | HF[b] | RB[e] |
|---|---|---|---|---|---|---|---|---|
| | Screening Results, % Control[a] | | | | | | | |
| 37 | 100 | 100 | 100 | 100 | 45/100 | A | 100 | A |
| 38 | 100 | 100 | 100 | 100 | 60/100 | A | 100 | — |
| 39 | 100 | 100 | 100 | 100 | 84/100 | A | — | — |
| 40 | 100 | 100 | 100 | 100 | 48/100 | A | — | — |
| 41 | 100 | 100 | 100 | 100 | 64/100 | A | — | — |
| 42 | 100 | 100 | 100 | 100 | 65/100 | A | — | A |
| 43 | 100 | 100 | 100 | 100 | 41/100 | A | — | — |
| 44 | 100 | 100 | 100 | 100 | 75/100 | A | — | — |
| 45 | 100 | 100 | 100 | 100 | 0/100 | A | 100 | — |
| 46 | 100 | 100 | 80 | 100 | 0/100 | A | 100 | — |
| 47 | 100 | 100 | 100 | 100 | 77/100 | A | 100 | — |
| 48 | 100 | 100 | 100 | 100 | 79/100 | A | — | B |
| 49 | 100 | 100 | 100 | 100 | 57/96 | A | — | — |
| 50 | 100 | 100 | 100 | 100 | 59/100 | A | — | — |
| 51 | 100 | 100 | 100 | 100 | 58/100 | A | 100 | A |
| 52 | 100 | 100 | 100 | 100 | 41/100 | A | 100 | A |
| 53 | 100 | 100 | 100 | 100 | 58/100 | A | — | — |
| 54 | 100 | 100 | 100 | 100 | 0/100 | A | 100 | A |
| 55 | 100 | 100 | 100 | 100 | 0/100 | A | 100 | — |
| 56 | 100 | 100 | 100 | 100 | 0/100 | A | 100 | A |
| 57 | 100 | 100 | 100 | 100 | 61/100 | A | 100 | — |
| 58 | 100 | 100 | 100 | 100 | 40/100 | A | 100 | — |
| 59 | 100 | 100 | 100 | 100 | 0/100 | A | 100 | A |
| 60 | 100 | 100 | 100 | 100 | 0/95 | A | 100 | A |
| 61 | 100 | 100 | 100 | 100 | 0/84 | A | 100 | A |
| 62 | 100 | 100 | 100 | 100 | 53/100 | A | 100 | A |
| 63 | 100 | 100 | 100 | 100 | 0/100 | A | — | — |
| 64 | 100 | 100 | 100 | 100 | 0/100 | A | 100 | — |
| 65 | 100 | 100 | 100 | 100 | 0/100 | A | 100 | — |
| 66 | 100 | 100 | 100 | 100 | 0/100 | A | 100 | — |
| 67 | 100 | 100 | 100 | 100 | 55/100 | A | 100 | — |
| 68 | 100 | 100 | 100 | 100 | 60/100 | A | 100 | B |
| 69 | 100 | 100 | 100 | 100 | 0/100 | A | — | — |
| 70 | 100 | 100 | 100 | 100 | 0/100 | A | 100 | B |
| 71 | 100 | 100 | 100 | 100 | 0/89 | A | 80 | — |
| 72 | 100 | 100 | 100 | 100 | 0/100 | A | 100 | B |
| 73 | 100 | 100 | 100 | 100 | 55/100 | A | 100 | — |
| 74 | 100 | 100 | 100 | 100 | 90/100 | C | — | — |
| 75 | 100 | 100 | 100 | 100 | 54/100 | C | — | — |
| 76 | 87 | 70 | 0 | 100 | 0/90 | C | — | — |
| 77 | 100 | 100 | 100 | 100 | 45/100 | C | — | — |
| 78 | 100 | 100 | 100 | 100 | 0/100 | C | 100 | — |
| 79 | 100 | 100 | 100 | 100 | 64/100 | A | 100 | E |
| 80 | 100 | 100 | 100 | 100 | 0/100 | — | — | — |
| 81 | 78 | 13 | 10 | 10 | 0/0 | C | O | E |

[a]TSM = two-spotted mite; GPA = green peach aphid; MBB = Mexican bean beetle; SAW = southern armyworm; CRW E/L = corn rootworm ova/larvae; nema = nematode; HF = housefly; RB = rice blast
[b]Insecticidal screening results, % control at 600 ppm
[c]Insecticidal screening results, % control at 150 ppm
[d]A = 0-9 knots on root; B = 10-25 knots on root; C = >25 knots on root (at 30 ppm in soil)
[e]Disease control: A = 97-100%; B = 90-96%; C = 70-89%; D = 50-69%; E = <50% (at 300 ppm)

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the phosphoramidates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual."

The phosphoramidates can be taken up or mixed with a finely particled solid carrier, as for example, clays, inorganic silicates, carbonates, and silicas. Organic carriers can also be employed. Dust concentrates are commonly made wherein phosphoramidates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphoramidates are usually present in the range of about 10 to about 35% by weight and surfactants from about 0.5 to about 10% by weight.

One convenient method for preparing a solid formulation is to impregnate the phosphoramidate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphoramidates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. Usually, this will involve the application of the phosphoramidate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose for such application, the phosphoramidate being utilized, the frequency of dissemination and the like.

By "agronomically acceptable carrier" is meant any substance which can be utilized to dissolve, disperse, or diffuse the chemical incorporated therein without impairing the effectiveness of the toxic agent and which does no permanent damage to such environment as soil, equipment and agronomic crops.

For use as insecticides and acaricides, dilute sprays can be applied at concentrations of about 0.01 to about 20 pounds of the phosphoramidate ingredient per 100 gallons of spray. They are usually applied at about 0.1 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a fungicide, the compounds of this invention can be applied as fungicidal sprays by methods commonly employed, such as, conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

For use as a nematocide, systemic agent, or as a soil insecticide, the phosphoramidates can be applied as a solid formulation, preferably a granular formulation or as a diluted liquid preparation, by broadcasting, side-dressing, soil incorporation or seed treatment.

The composition can also be added to transplant water or employed as dips or soaks for vegetative parts employed in propagation, such as seeds, tubers, roots, seedlings, etc., so as to disinfect and/or provide residual protection from nematodes, soil insects (and mites) and via systemic uptake, foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil at a rate of about 1 to about 100 p.p.m. of active ingredient.

The compounds of this invention can be utilized as the sole pesticidal agents or they can be employed in conjunction with other bactericides, fungicides, herbicides, insecticides, acaricides, nematocides and comparable pesticides.

Many variations of this invention are possible without departing from the spirit or scope thereof.

We claim:

1. A compound of the formula

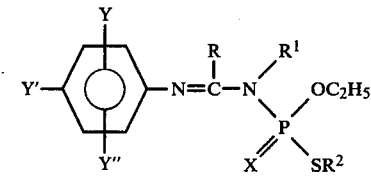

wherein Y, Y', Y'' are independently hydrogen, $(C_1-C_6)$-alkyl, halogen, $(C_1-C_6)$alkoxy, $(C_1-C_6)$-alkylthio, nitro, cyano, $(C_1-C_6)$alkoxy-carbonyl, di$(C_1-C_4)$alkylamino, $(C_1-C_6)$-alkylcarbonyl, di$(C_1-C_4)$alkylaminocarbonyl, arylthio, or aryloxy;

R is hydrogen, $(C_1-C_6)$alkyl, di$(C_1-C_4)$-alkylamino, $(C_1-C_6)$alkoxy, $(C_1-C_6)$-alkylthio or cyano;

$R^1$ is
(a) substituted $(C_1-C_6)$alkyl;
(b) optionally substituted $(C_3-C_8)$ cycloalkyl;
(c) optionally substituted $(C_3-C_6)$alkenyl;
(d) optionally substituted $(C_5-C_8)$cycloalkenyl;
(e) $(C_3-C_6)$alkynyl; or
(f) optionally substituted aralkyl with up to 11 carbons, $R^2$ is $(C_3-C_4)$alkyl; and X is oxygen or sulfur.

2. A compound according to claim 1 wherein R is hydrogen.

3. A compound according to claim 1 wherein R is hydrogen, $(C_1-C_4)$alkyl, di$(C_1-C_4)$alkylamino, , $(C_1-C_4)$alkoxy, $(C_1-C_4)$alkylthio, or cyano;
$R^2$ is $(C_3-C_4)$alkyl;
$R^3$ is $(C_3-C_4)$alkyl.

4. A compound according to claim 3 wherein R is hydrogen or $(C_1-C_4)$alkyl.

5. A compound according to claim 4 wherein Y, Y', Y'' are independently hydrogen, $(C_1-C_4)$-alkyl, cyano, halogen, nitro, $(C_1-C_4)$-alkylthio, di$(C_1-C_3)$alkylamino, $(C_1-C_4)$alkoxy, phenylthio, or phenoxy;
$R^1$ is, $(C_1-C_3)$cyanoalkyl, $(C_1-C_3)$-phenylthioalkyl, $(C_1-C_4)$alkoxycarbonylalkyl $(C_1-C_3)$, , $(C_3-C_4)$alkenyl, $(C_3-C_4)$-alkynyl; $(C_5-C_7)$cycloalkyl, $(C_3-C_4)$alkenyl-oxyalkyl$(C_1-C_3)$, $(C_7-C_9)$aralkyl, or $(C_3-C_4)$-alkenyloxycarbonylalkyl $(C_1-C_3)$.

6. A compound according to claim 5 wherein Y, Y', Y'' are independently hydrogen, methyl, chlorine, methylthio, or nitro.

7. A compound according to claim 3 wherein R is $(C_1-C_3)$alkyl; di$(C_1-C_3)$alkylamino, , or $(C_1-C_3)$alkoxy.

8. A compound of the formula

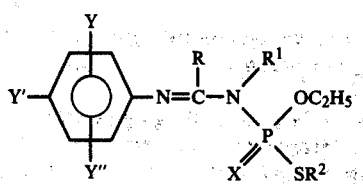

wherein

Y, Y',Y'' are independently hydrogen, $(C_1-C_6)$-alkyl, halogen, $(C_1-C_6)$alkoxy, $(C_1-C_6)$-alkylthio, nitro, cyano, $(C_1-C_6)$alkoxycarbonyl, $di(C_1-C_4)$alkylamino, $(C_1-C_6)$-alkylcarbonyl, $di(C_1-C_4)$alkylaminocarbonyl, arylthio, or aryloxy;

R is hydrogen, $(C_1-C_6)$alkyl, $di(C_1-C_4)$-alkylamino, $(C_1-C_6)$alkoxy, $(C_1-C_6)$-alkylthio or cyano;

$R^1$ is unsubstituted $(C_1-C_6)$alkyl;

$R^2$ is $(C_3-C_4)$alkyl; and

X is oxygen or sulfur.

9. A compound according to claim 8 wherein R is a substituent other than hydrogen.

10. A compound according to claim 8 wherein Y, Y', Y'' are hydrogen.

11. A compound according to claim 8 wherein Y, Y', Y'' are independently hydrogen, methyl, chlorine, methylthio, or nitro.

12. A compound according to claim 11 wherein R is hydrogen, $(C_1-C_3)$alkyl, $di(C_1-C_3)$alkylamino, or $(C_1-C_3)$-alkoxy.

13. A compound according to claim 8 wherein Y' is methyl or chlorine and Y and Y'' are substituents other than methyl or chlorine.

14. A compound according to claim 1 wherein

R is hydrogen, $(C_1-C_4)$alkyl, $di(C_1-C_4)$ alkylamino, $(C_1-C_4)$alkoxy, $(C_1-C_6)$alkylthio, or cyano;

$R^1$ is
 (a) substituted $(C_1-C_4)$alkyl,
 (b) optionally substituted $(C_5-C_7)$-cycloalkyl
 (c) optionally substituted $(C_3-C_4)$-alkenyl,
 (d) optionally substituted $(C_5-C_8)$-cycloalkenyl,
 (e) $(C_3-C_4)$alkynyl, or
 (f) $(C_7-C_9)$aralkyl.

15. A compound according to claim 8 wherein R is hydrogen.

16. A compound according to claim 1 having the formula

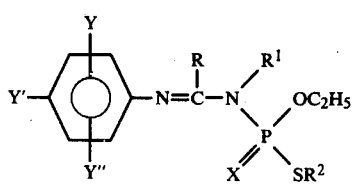

wherein

R is hydrogen, or $(C_1-C_4)$alkyl;

$R^1$ is cyclohexyl, $(C_3-C_4)$alkenyl, propargyl, phenylthio $(C_1-C_4)$alkyl, cyano $(C_1-C_4)$alkyl, $(C_1-C_4)$alkoxy carbonyl $(C_1-C_4)$alkyl, or benzyl;

Y, Y', Y'' are independently hydrogen, methyl, chlorine, nitro or methylthio.

17. A compound according to claim 12 having the formula

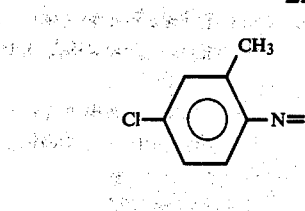

wherein
$R^2$ is n-propyl or iso-butyl.

18. A compound according to claim 12 having the formula

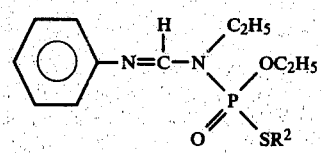

wherein
$R^2$ is n-propyl or sec-butyl.

19. A compound according to claim 16 having the formula

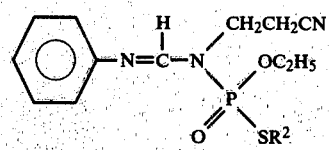

wherein
$R^2$ is n-propyl or sec-butyl.

20. A compound according to claim 16 having the formula

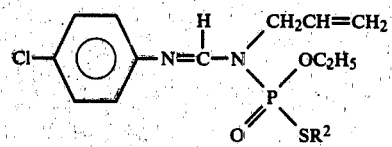

wherein
$R^2$ is n-propyl or sec-butyl.

21. A compound according to claim 12 having the formula

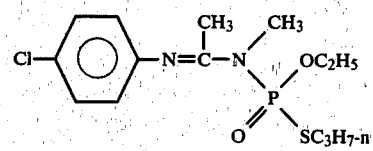

22. A pesticidal composition comprising a compound according to claim 1 and an agronomically acceptable carrier.

23. A pesticidal composition comprising a compound according to claim 2 and an agronomically acceptable carrier.

24. A method of controlling pests, wherein the pests are fungi, arthropods and nematodes, which comprises applying directly to the pests or to the loci to be freed of or protected from attack by the pests, a pesticidally effective amount of a compound of claim 1.

25. A method of controlling pests, wherein the pests are fungi, arthropods and nematodes, which comprises applying directly to the pests or to the loci to be freed of or protected from attack by the pests, a pesticidally effective amount of a compound of claim 2.

26. A method of controlling pests which comprises applying directly to the pests or to the loci to be freed of or protected from attack by the pests, a pesticidally effective amount of a composition of claim 22.

27. A method according to claim 26 wherein the pests are phytopathogenic fungi.

28. A method according to claim 27 wherein the fungi are rice blast.

29. A method according to claim 26 wherein the pests are arthropods.

30. A method of controlling pests which comprises applying directly to the pests or to the loci to be freed of or protected from attack by the pests, a pesticidally effective amount of a composition of claim 23.

31. A method according to claim 30 wherein the pests are nematodes.

32. A pesticidal composition comprising a compound according to claim 8 and an agronomically acceptable carrier.

33. A pesticidal composition comprising a compound according to claim 15 and an agronomically acceptable carrier.

34. A method of controlling pests, wherein the pests are fungi, arthropods and nematodes, which comprises applying directly to the pests or to the loci to be freed of or protected from attack by the pests, a pesticidally effective amount of a compound of claim 8.

35. A method of controlling pests which comprises applying directly to the pests or to the loci to be freed of or protected from attack by the pests a pesticidally effective, amount of a composition of claim 32.

36. A method of controlling pests which comprises applying directly to the pests or to the loci to be freed of or protected from attack by the pests, a pesticidally effective amount of a composition of claim 33.

37. A method according to claim 36 wherein the pests are nematodes.

* * * * *